US012150969B2

(12) United States Patent
Li et al.

(10) Patent No.: US 12,150,969 B2
(45) Date of Patent: Nov. 26, 2024

(54) SYNTHETICALLY ENVELOPED VIRUS

(71) Applicant: University of Pittsburgh—Of the Commonwealth System of Higher Education, Pittsburgh, PA (US)

(72) Inventors: Song Li, Wexford, PA (US); Stephen Howard Thorne, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 691 days.

(21) Appl. No.: 16/088,228

(22) PCT Filed: Mar. 24, 2017

(86) PCT No.: PCT/US2017/023948
§ 371 (c)(1),
(2) Date: Aug. 12, 2020

(87) PCT Pub. No.: WO2017/165725
PCT Pub. Date: Sep. 28, 2017

(65) Prior Publication Data
US 2020/0316146 A1    Oct. 8, 2020

Related U.S. Application Data

(60) Provisional application No. 62/313,270, filed on Mar. 25, 2016.

(51) Int. Cl.
*A61K 35/76*    (2015.01)
*A61K 9/127*    (2006.01)
(Continued)

(52) U.S. Cl.
CPC ............ *A61K 35/76* (2013.01); *A61K 9/1271* (2013.01); *A61K 47/10* (2013.01); *A61K 47/24* (2013.01);
(Continued)

(58) Field of Classification Search
None
See application file for complete search history.

(56) References Cited

U.S. PATENT DOCUMENTS 2,544,772 A * 3/1951 Audrieth ................ C09K 23/14
508/389
10,113,151 B2 * 10/2018 Kummel ................. A61P 35/00
(Continued)

FOREIGN PATENT DOCUMENTS

WO    WO2013152227 A1    10/2013
WO    WO2014070659 A1    5/2014
(Continued)

OTHER PUBLICATIONS

Liu et al (Viruses, 2014, 6, 3787-3808). (Year: 2014).*
(Continued)

*Primary Examiner* — Celeste A Roney
(74) *Attorney, Agent, or Firm* — BARTONY & ASSOCIATES LLC

(57) ABSTRACT

A method of modifying a virus for in vivo delivery to a region of interest includes forming an enveloping composition including a lipid conjugate formed by conjugating at least one lipid with at least one hydrophilic compound via a linkage which is cleavable under conditions present in the region of interest and combining the virus with the enveloping composition to encompass the virus within the enveloping structure.

28 Claims, 9 Drawing Sheets

(51) Int. Cl.
  *A61K 47/10* (2017.01)
  *A61K 47/24* (2006.01)
  *A61K 47/28* (2006.01)
  *A61K 47/34* (2017.01)
  *A61K 47/69* (2017.01)
  *A61P 35/00* (2006.01)

(52) U.S. Cl.
  CPC .............. *A61K 47/28* (2013.01); *A61K 47/34* (2013.01); *A61K 47/6911* (2017.08); *A61P 35/00* (2018.01)

(56) References Cited

U.S. PATENT DOCUMENTS

| | | | |
|---|---|---|---|
| 2007/0086984 A1* | 4/2007 | Coffey | A61K 35/76 424/93.2 |
| 2011/0070164 A1 | 3/2011 | Dangerfield | |
| 2012/0258540 A1* | 10/2012 | LeDoux | C12N 15/87 435/235.1 |
| 2013/0202686 A1* | 8/2013 | Yamashita | A61K 9/127 424/450 |
| 2015/0231271 A1 | 8/2015 | Li | |
| 2015/0306034 A1 | 10/2015 | Gao | |
| 2017/0246288 A1* | 8/2017 | Li | A61K 39/001182 |

FOREIGN PATENT DOCUMENTS

| | | | | |
|---|---|---|---|---|
| WO | WO-2015027163 A1 * | 2/2015 | ........... | A61K 35/768 |
| WO | WO2015167408 A1 | 11/2015 | | |
| WO | WO2017165725 A8 | 9/2017 | | |

OTHER PUBLICATIONS

Zhang et al (ACS Macro Lett, 2015, 4(6), 620-623) (Year: 2015).*
Li et al (Bioconjugate Chem, 2014, 25, 1689-96) (Year: 2014).*
Cabral, H.; Matsumoto, Y.; Mizuno, K.; Chen, Q.; Murakami, M.; Kimura, M.; Terada, Y.; Kano, M. R.; Miyazono, K.; Jesaka, M.; Nishiyama, N.; Kataoka, K., Accumulation of sub-100 nm polymeric micelles in poorly permeable tumours depends on size; Nat. Nanotechnol. 2011, 6, 815-823.
Torchilin, V. P. Micellar nanocarriers: pharmaceutical perspectives; Pharm. Res. 2007, 24, 1-16.
Bae, Y .; Fukushima, S.; Harada, A.; Kataoka, K., Design of environment-sensitive supramolecular assemblies for Intracellular drug delivery: polymeric micelles that are responsive to intracellular pH change, Angew. Chem. Int. Ed. Engl. 2003. 42, (38), 4640-3.
Sankaranarayanan, J.; Mahmoud, E. A.; Kim, G.; Morachis, J. M.; Almutairi, A., Multiresponse strategies to modulate purst degradation and release from nanoparticles, ACS nano 2010, 4, 5930-5936.
Chen, J.; Zhao, M.; Feng, F.; Sizovs, A.; Wang, J.; Tunable Thioesters as "Reduction" Responsive Functionality for Traceless Reversible Protein PEGylation; J. Am. Chem. Soc. 2013, 135, 10938-10941.
Aguirre-Chagala, Yanet. E.; Santos, J. L.; Huang, Y. X.; Herrera-Alonso, M.; Phenylboronic Acid-Installed Polycarbonates for the pH-Dependent Release of Diol-Containing Molecules; Acs Macro Lett. 2014, 3, 1249-1253.
Wei, H.; Zhuo, R. X.; Zhang, X. Z.; Design and development of polymeric micelles with cleavable links for intracellular drug delivery; Prog. Polym. Sci. 2013, 38, 503-535.
Howard, M. D.; Ponta, A.; Eckman, A.; Jay, M.; Bae, Y., Polymer micelles with hydrazone-ester dual linkers for tunable release of dexamethasone; Pharm. Res. 2011, 28, 2435-2446.
Du, J. Z.; Du, X. J.; Mao, C. Q.; Wang, J. J. Tailor-made dual pH-sensitive polymer-doxorubicin nanoparticles for efficient anticancer drug delivery; Am. Chem. Soc. 2011, 133, 17560-17563.
Bae, Y.; Nishiyama, N.; Fukushima, S.; Koyama, H.; Yasuhiro, M.; Kataoka, K.; Preparation and biological characterization of polymeric micelle drug carriers with intracellular pH-triggered drug release property: tumor permeability, controlled subcellular drug distribution, and enhanced in vivo antitumor efficacy; Bioconjug. Chem. 2005, 16, 122-30.
Li, S. Y.; Liu, L. H.; Jia, H. Z.; Qiu, W. X.; Rong, L.; Cheng, H.; Zhang, X. Z.; A pH-responsive prodrug for real-time drug release monitoring and targeted cancer therapy; Chem. Commun. 2014, 50, 11852-11855.
Zhang, X.; Lu, J.; Huang, Y.; Zhao, W.; Chen, Y.; Li, J.; Gao, X.; Venkataramanan, R.; Sun, M.; Stolz, D. B.; Zhang, L.; Li, S.; PEG-farnesylthiosalicylate conjugate as a nanomicellar carrier for delivery of paclitaxel; Bioconjug. Chem. 2013, 24, 464-72.
Zhang, X.; Huang, Y.; Zhao, W.; Chen, Y.; Zhang, P.; Li, J.; Venkataramanan, R.; Li, S.; PEG-farnesyl thiosalicylic acid telodendrimer micelles as an improved formulation for targeted delivery of paclitaxel; Mol. Pharm.2014, 11, 2807-14.
Chen, Y.; Zhang, X.; Lu, J.; Huang, Y.; Li, J.; Li, S.; Targeted delivery of curcumin to tumors via PEG-derivatized FTS-based micellar system; AAPS J. 2014, 16, No. 3, 600-608.
Zhang, X.; Huang, Y.; Zhao, W.; Liu, H.; Marquez, R.; Lu, J.; Zhang, P.; Zhang, Y.; Li, J.; Gao, X.; Venkataramanan, R.; Xu, L.; Li, S.; Targeted delivery of anticancer agents via a dual function nanocarrier with an interfacial drug-interactive motif, Biomacromolecules 2014, 15, 4326-35.
Zhang, X.; Liu, K.; Huang, Y.; Xu, J.; Li, J.; Ma, X.; Li, S.; Reduction-sensitive dual functional nanomicelles for improved delivery of paclitaxel; Bioconjug. Chem. 2014, 25, 1689-96.
Marom, M.; Haklai, R.; Ben-Baruch, G.; Marciano, D.; Egozi, Y.; Kloog, Y. J.; Selective inhibition of Ras-dependent cell growth by farnesylthiosalisylic acid; Biol. Chem. 1995, 270, 22263-22270.
Haklai, R.; Weisz, M. G.; Elad, G.; Paz, A.; Marciano, D.; Egozi, Y.; Ben-Baruch, G.; Kloog, Y.; Dislodgment and accelerated degradation of Ras; Biochemistry 1998, 37, 1306-1314.
Marciano, D.; Benbaruch, G.; Marom, M.; Egozi, Y.; Haklai, R.; Kloog, Y.; Farnesyl derivatives of rigid carboxylic acids-inhibitors of ras-dependent cell growth; J. Med. Chem. 1995, 38, 1267-1272.
Blum, R.; Kloog, Y.; Tailoring Ras-pathway-inhibitor combinations for cancer therapy; Drug Resist. Updat. 2005, 8, 369-380.
Gana-Weisz, M.; Halaschek-Wiener, J.; Jansen, B.; Elad, G.; Haklai, R.; Kloog, Y.; The Ras inhibitor S-trans, trans-farnesylthiosalicylic acid chemosensitizes human tumor cells without causing resistance; Clin. Cancer Res. 2002, 8, 555-565.
Mackenzie, G. G.; Bartels, L. E.; Xie, G.; Papayannis, I.; Alston, N.; Vrankova, K.; Ouyang, N.; Rigas, B.; A novel Ras Inhibitor (MDC-1016) reduces human pancreatic tumor growth in mice; Neoplasia 2013, 15, No. 10, 1184-1195.
Mor, A.; Aizman, E.; Chapman, J.; Kloog, Y.; Immunomodulatory properties of farnesoids: the new steroids? Current Med. Chem. 2013, 20, 1218-1224.
Goldberg, L.; Haklai, R.; Bauer, V.; Heiss, A.; Kloog, Y.; New Derivatives of Farnesylthiosalicylic Acid (Salirasib) for Cancer Treatment: Farnesylthiosalicylamide Inhibits Tumor Growth in Nude Mice Models; J. Med. Chem. 2009, 52, 197-205.
Ling, Y.; Wang, Z.; Zhu, H.; Wang, X.; Zhang, W.; Wang, X.; Chen, L.; Huang, Z.; Zhang, Y.; Synthesis and biological evaluation of farnesylthiosalicylamides as potential anti-tumor agents; Bioorg. Med. Chem. 2014, 22, 374-380.
Kale, A. A. et al., "Design, Synthesis and Characterization of pH-Sensitive PEG-PE Conjugates for Stimuli-Sensitive Pharmaceutical Nanocarriers: The Effect of Substitutes at the Hydrazone Linkage on the pH-Stability of PEG-PE nonjugates", Bioconjug Chem., 2007, vol. 18, No. 2, pp. 363-370.
Wan, Yu et al., Enzyme-responsive liposomes modified adenoviral vectors for enhanced tumor cell transduction and reduced immunogenicity; Biomaterials; vol. 34; No. 12; Jan. 27, 2013; pp. 3020-3030.
Zhang, Xiaolan et al.; Tunable pH-Responsive Polymeric Micelle for Cancer Treatment; ACS Macro Letters; vol. 4; No. 6; May 18, 2015; pp. 620-623.
Extended European Search Report and Written Opinion mailed on Oct. 14, 2019 of the counterpart European patent application No. 17771210.6.

* cited by examiner

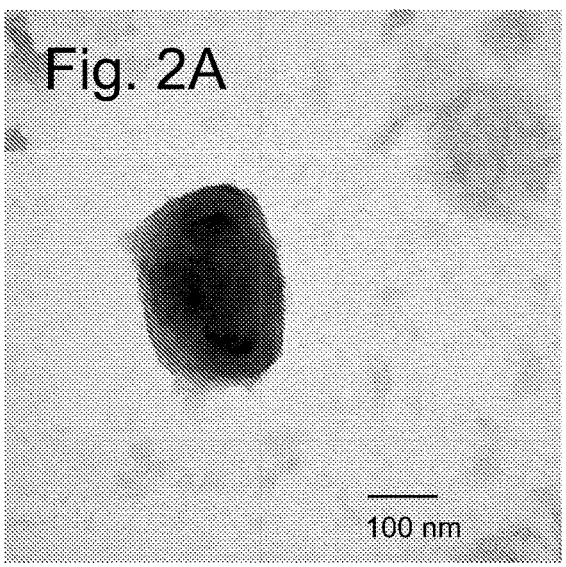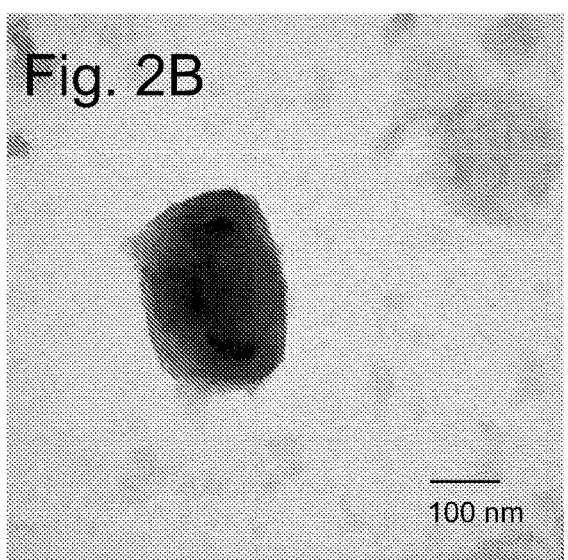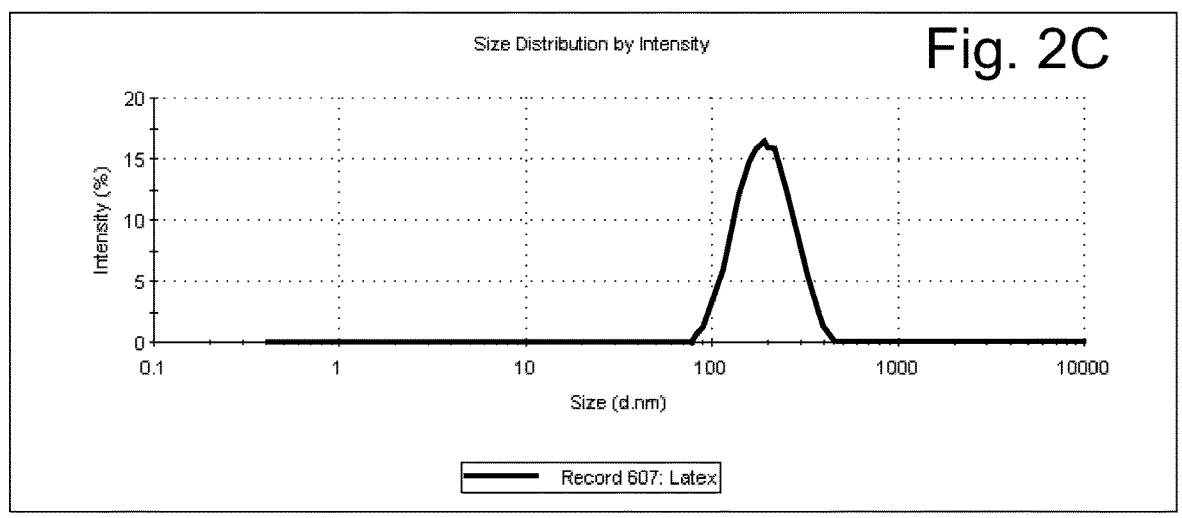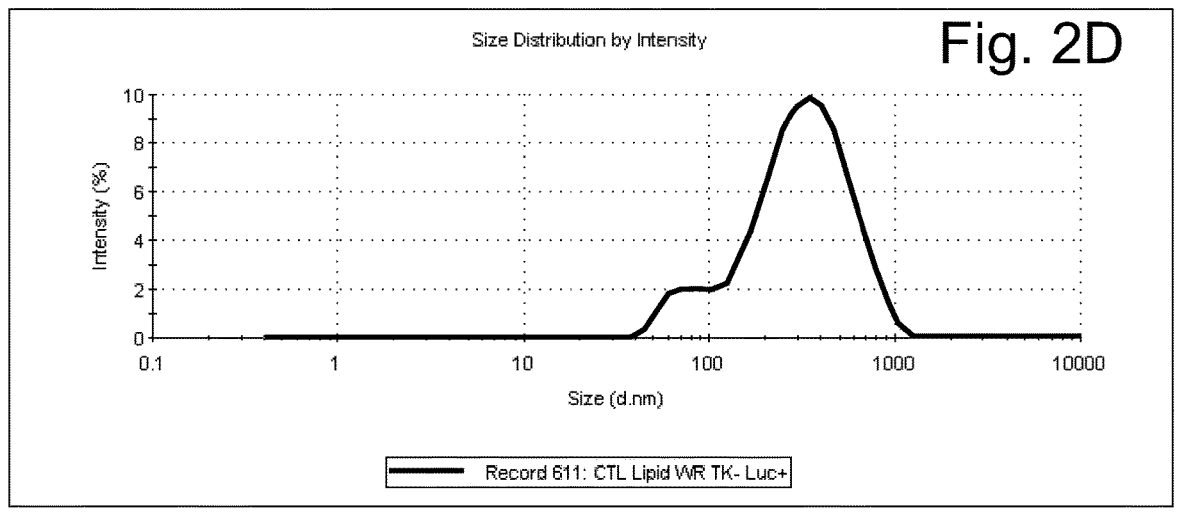

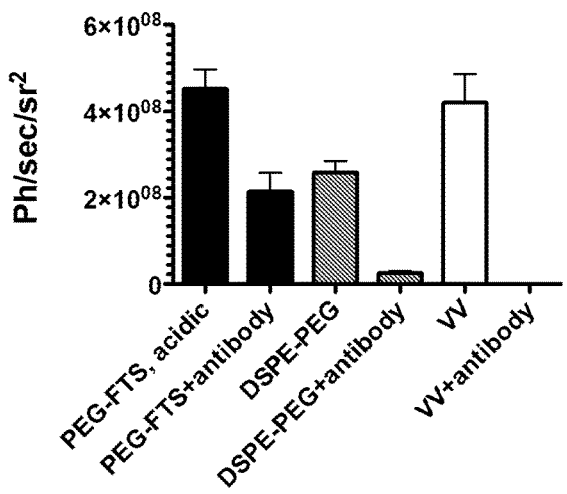
Fig. 3
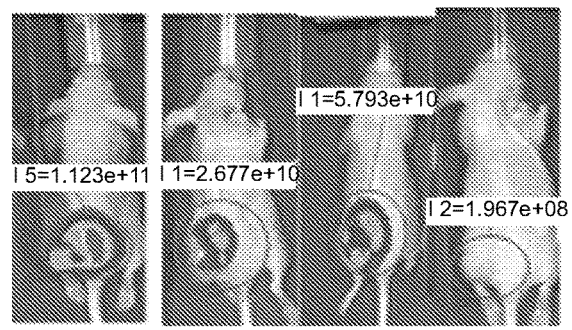
Fig. 4A
eVV = enveloped Virus
NuAb = anti-viral neutralizing Antibody
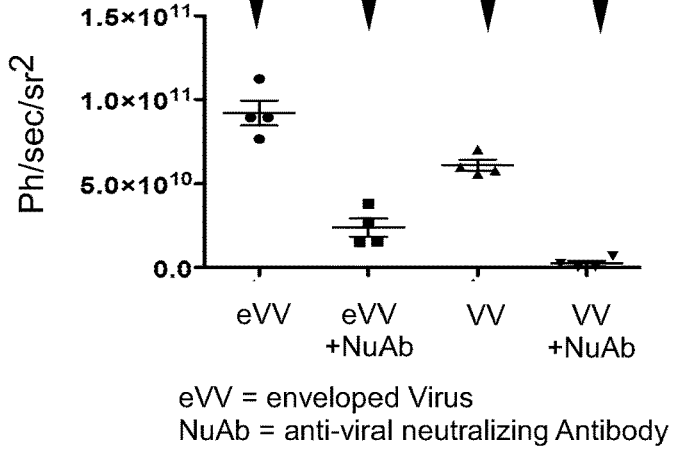
Upper body Signal (12h)
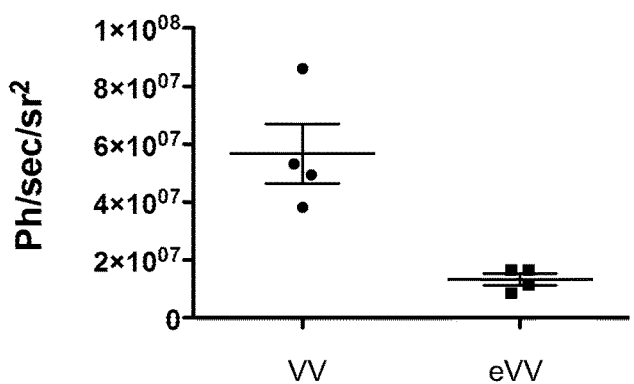
Fig. 4B

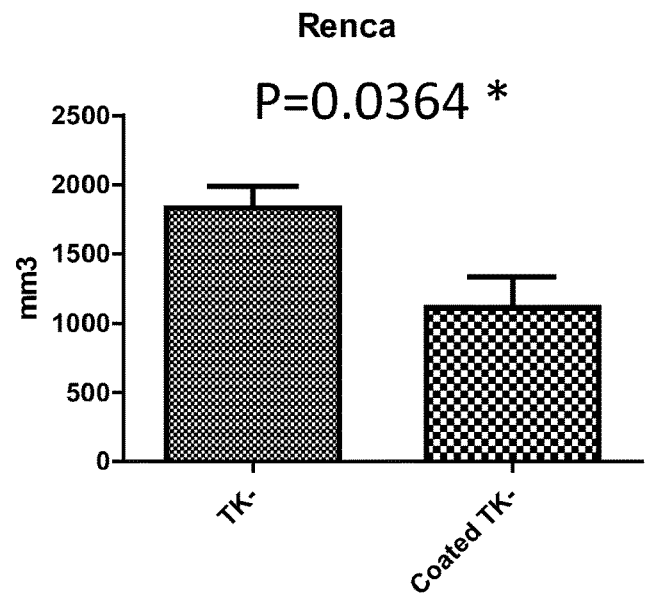
Fig. 6A  3 Days between treatments
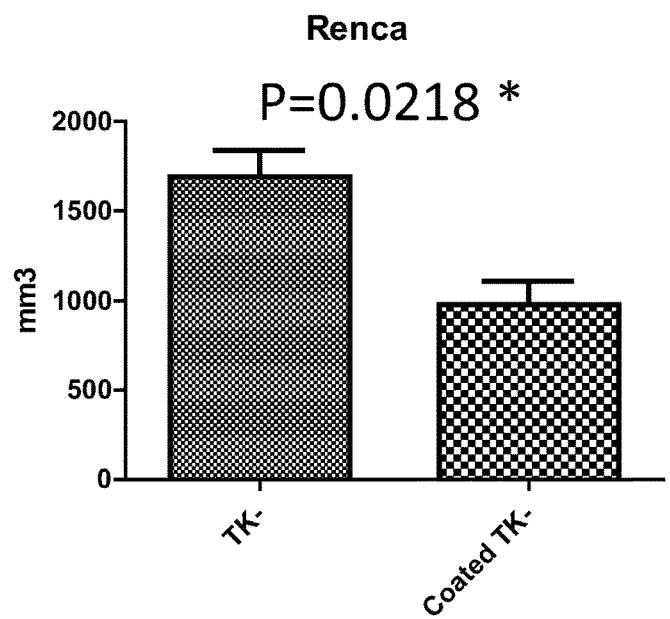
Fig. 6B  14 Days between treatments

SYNTHETICALLY ENVELOPED VIRUS

CROSS-REFERENCE TO RELATED APPLICATIONS

This application is a national phase filing of PCT International Patent Application No. PCT/US2017/023948, filed Mar. 24, 2017, which claims benefit of U.S. Provisional Patent Application Ser. No. 62/313,270, filed Mar. 25, 2016, the disclosures of which are incorporated herein by reference.

GOVERNMENTAL INTEREST

This invention was made with government support under grant no. CA140215 awarded by the National Institutes of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Viral therapies or virotherapies are treatment regimens in which biotechnology is used to convert viruses into therapeutic agents by reprogramming the viruses to treat diseases. Currently, there are three primary branches of viral therapies including anti-cancer or oncolytic viruses, viral immunotherapy and viral vectors for gene therapy.

Rationally designed and engineered oncolytic viral (OV) therapies were first tested in the clinic over 25 years ago. However, it is only in the last five years that clinical responses have begun to approach the promise shown in pre-clinical models. The demonstration of enhanced responses and/or survival seen in randomized clinical testing with several vectors, including talimogene laherparepvec (T-Vec), pexastimogene devacirepvec (Pexa-Vec) and coxsackievirus A21 (CVA21) indicated that US Food and Drug Administration (FDA) approval will likely be forthcoming for one or more vectors in different indications. The administration of T-Vec for metastatic melanoma has, for example, recently been approved by the US FDA. However, all of those trials have relied on direct intratumoral injection. Disseminated disease is the major cause of cancer-related death and cannot be adequately treated with intratumoral injections. In addition, because an initial round of treatment raises an immune response against the therapy itself, subsequent cycles or treatment are further limited in their ability to achieve systemic delivery. Although the possibility for systemic OV delivery, even leading to remission of disseminated disease, has been demonstrated in the clinic, such case reports merely act to highlight the future potential of the field if reliable and reproducible systemic delivery could be achieved.

A variety of different approaches have been proposed to try to overcome limitations in systemic treatment via an OV or other viral vector. Approaches involving immunosuppression of the cancer patient have largely been abandoned as it has become clear that the immunotherapeutic effects of OV vectors are an important component to their tumor-killing potential. Sequential use of related but serologically distinct vectors and the use of pre-infected cells as delivery vehicles have met with some success, but add to the complexity and cost of the therapy. Use of intratumoral or local-regional delivery can be used in some limited settings, but typically fail to treat widespread metastatic disease. Even if the OV therapy is capable of raising an adaptive immune response targeting tumor antigens, metastases are often antigenicaly distinct from the primary tumor.

Approaches that involve chemical modifications of the viral particle itself show theoretical promise. Such modifications involve direct chemical attachment of large inert molecules (such as PEG) to the viral particle, or the addition of a lipid envelope or polymer-based coating around the particle. Although a number of such approaches have demonstrated the capacity to protect the viral particle and/or detarget the virus from natural target tissues (particularly the liver), such approaches commonly disrupt the virus's evolved pathways of cell entry and thereby limit the ability of the virus to infect tumor cells. The use of cationic polymers that are pH sensitive may mitigate this limitation, but have raised toxicity concerns. Although there is a great need for technologies in which the viral particle is modified, none have advanced into a clinical setting to date.

SUMMARY

In one aspect, a method of modifying a virus for in vivo delivery to a region of interest includes forming an enveloping composition including a lipid conjugate formed by conjugating at least one lipid with at least one hydrophilic compound via a linkage which is cleavable under conditions present in the region of interest and combining the virus with the enveloping composition to encompass the virus within the structure. The enveloping composition may, for example, form a lipid bilayer to encompass/envelope the virus.

In a number of embodiments, the at least one lipid is selected from the group consisting of n-docosanoic acid, arachidic acid, stearic acid, palmitic acid, myristic acid, lauric acid, oleyl acid, vitamin E, embelin, 1-phenyl-2-palmitoylamino-3-morpholino-1-propanol, or a compound having the formula:

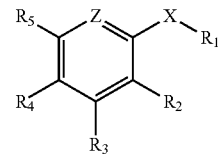

wherein $R_1$ is a farnesyl group, a geranyl group or geranylgeranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group, or derivative thereof. In a number of embodiment, the at least one lipid has the formula:

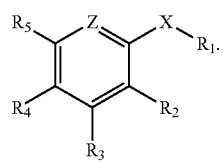

The at least one lipid may, for example, be selected from the group consisting of S-trans, trans-farnesylthiosalicylic acid, S-trans, trans-farnesylthiosalicylic acid amide (FTS-amide), S-trans, trans-farnesylthiosalicylic acid methylamide (FTS-MA) and S-trans, trans-farnesylthiosalicylic acid dimethylamide (FTS-DMA). In a number of embodiments, the at least one lipid is farnesylthiosalicylic acid or a farnesylthiosalicylic acid amide.

In a number of embodiments, a family of the virus is selected from the group consisting of poxvidrae, denoviridae, herpesviridae, picornaviridae, rhabdoviridae, paramyxoviridae, retroviridae, togaviridae or reoviridae. The virus may, for example, be selected from the group consisting of a vaccinia virus, a myxoma virus, an avipox virus, an adenovirus, a herpes simplex virus (HSV) coxsackie virus, a vesicular stomatitis virus (VSV), a Newcastle disease virus (NDV), an adeno-associated virus (AAV), a polio virus, a lenti virus, a retrovirus, a reovirus, or a sindbis virus. In a number of embodiments, the family of the virus is poxvidrae. The virus may, for example, be a vaccinia virus. The virus may, for example, be a mature vaccinia virus.

In a number of embodiments, the region of interest includes a tumor, and the virus is modified to treat the tumor.

In a number of embodiments, the at least one hydrophilic compound includes at least one hydrophilic oligomer or at least one hydrophilic polymer. The hydrophilic oligomer or the hydrophilic polymer may, for example, be selected from the group consisting of a polyalkylene oxide, a polyvinylalcohol, a polyacrylic acid, a polyacrylamide, a polyoxazoline, a polysaccharide and a polypeptide. In a number of embodiments, the at least one hydrophilic compound is a polyalkylene oxide. The polyalkylene oxide may, for example, be a polyethylene glycol. A polyethylene glycol or other hydrophilic polymer may, for example, have a molecular weight of at least 1 KDa.

In a number of embodiments, the linkage is sensitive to pH. The linkage may, for example, include a hydrazine group.

The enveloping composition may include at least one co-lipid. The at least one co-lipid may, for example, be a phospholipid. The method may further include providing an additive in the enveloping composition. The additive may, for example, increase or decrease stability of the enveloping composition. Cholesterol may, for example, be included as an additive. DOPE (1,2-dioleoyl-sn-glycero-3-phosphoethanolamine) is a fusogenic lipid, which may be used to decrease the lipid stability and facilitate the release of virus.

In another aspect, a formulation (for example, for in vivo delivery to a region of interest) includes a virus, a synthetic enveloping composition (as described above) encompassing the virus and including a lipid conjugate formed by conjugating at least one lipid with at least one hydrophilic compound via a linkage which is cleavable under conditions present in the region of interest. As described above, the enveloping composition may a lipid bilayer encompassing the virus.

In another aspect, a method of in vivo delivery of a virus to a region of interest includes injecting a formulation as described above.

In another aspect, a method of modifying a virus for in vivo delivery to a region of interest includes forming an enveloping composition includes a lipid having the formula:

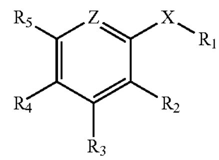

wherein $R_1$ is a farnesyl group, a geranyl group or geranyl-geranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group, or derivative thereof, and combining the virus with the enveloping composition to encompass the virus. The enveloping composition may from a lipid bilayer. The lipid may, for example, be selected from the group consisting of S-trans, trans-farnesylthiosalicylic acid, S-trans, trans-farnesylthiosalicylic acid amide (FTS-amide), S-trans, trans-farnesylthiosalicylic acid methylamide (FTS-MA) and S-trans, trans-farnesylthiosalicylic acid dimethylamide (FTS-DMA).

The enveloping composition forms a lipid bilayer. In a number of embodiments, the lipid is selected from the group consisting of S-trans, trans-farnesylthiosalicylic acid, S-trans, trans-farnesylthiosalicylic acid amide (FTS-amide), S-trans, trans-farnesylthiosalicylic acid methylamide (FTS-MA) and S-trans, trans-farnesylthiosalicylic acid dimethylamide (FTS-DMA).

The enveloping composition may, for example, include at least one co-lipid. The at least one co-lipid may, for example, be a phospholipid. The method may further include providing an additive in the enveloping composition. The additive may, for example, increase or decrease stability of the enveloping composition. Cholesterol may, for example, be included as an additive.

In a further aspect, embodiment a formulation (for example, for in vivo delivery to a region of interest) includes a virus, a synthetic enveloping composition encompassing the virus and comprising a lipid having the formula:

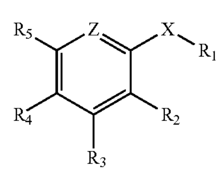

wherein $R_1$ is a farnesyl group, a geranyl group or geranyl-geranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group, or derivative thereof. The enveloping composition may be further characterized as described above.

In still a further aspect a composition is formed by conjugating at least one lipid with at least one hydrophilic compound via a pH-sensitive hydrazine linkage which is cleavable under conditions present in the region of interest. The composition may, for example, form a lipid bilayer. The at least one lipid may, for example, be selected from the group consisting of n-docosanoic acid, arachidic acid, stearic acid, palmitic acid, myristic acid, lauric acid, oleyl acid, vitamin E, embelin, 1-phenyl-2-palmitoylamino-3-morpholino-1-propanol, or a compound having the formula:

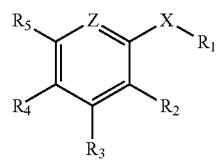

wherein $R_1$ is a farnesyl group, a geranyl group or geranylgeranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group, or derivative thereof. In a number of embodiments, the at least one lipid has the formula:

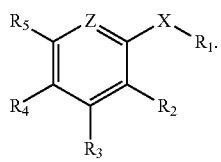

The at least one lipid may, for example, be selected from the group consisting of S-trans, trans-farnesylthiosalicylic acid, S-trans, trans-farnesylthiosalicylic acid amide (FTS-amide), S-trans, trans-farnesylthiosalicylic acid methylamide (FTS-MA) and S-trans, trans-farnesylthiosalicylic acid dimethylamide (FTS-DMA). In a number of embodiments, the at least one lipid is farnesylthiosalicylic acid or a farnesylthiosalicylic acid amide (or a biologically active derivative thereof).

The at least one hydrophilic compound may, for example, include at least one hydrophilic oligomer or at least one hydrophilic polymer. The hydrophilic oligomer or the hydrophilic polymer may, for example, be selected from the group consisting of a polyalkylene oxide, a polyvinylalcohol, a polyacrylic acid, a polyacrylamide, a polyoxazoline, a polysaccharide and a polypeptide. In a number of embodiments, the at least one hydrophilic compound is a polyalkylene oxide. The polyalkylene oxide may, for example, be a polyethylene glycol. The polyethylene glycol or other hydrophilic polymer may, for example, be a molecular weight of at least 1 KDa. In a number of embodiments, the linkage is sensitive to pH.

The synthetic lipid-derived liposomal envelopes or enveloping compositions hereof create an enveloped virus with dramatically improved therapeutic potential and novel properties. The synthetically enveloped virus retains (and in some cases even increases) infectivity of the virus over non-enveloped virus. The synthetically enveloped virus may increase absolute infection (as determined by viral gene expression) in a target tissue (tumor) in vivo relative to a non-enveloped virus.

Delivery of synthetically enveloped virus to tumors via an intravenous route may be inefficient as a result of its rapid clearance by the reticuloendothelial system (RES). This problem may be resolved, however, through covalent attachment of hydrophilic chemical structures, which may, for example, be inert, (such as polyethylene glycol) to the lipid envelope, using bonds that may be cleaved under particular environmental conditions (such as low pH, REDOX potential, presence of proteases etc.). As used herein, the term "inert" refers to hydrophilic chemical structures (for example, polymers) that do not have significant biological effects other than the intended shielding effect. In this manner, the viral vectors may be further detargeted and protected while in circulation. Release of the synthetic enveloped virus from the hydrophilic outer shell can be made conditional on the target microenvironment (such as low pH typically found in the tumor, increased oxidative stress found in inflammation etc.). Addition of other targeting factors into the synthetic may also be used to target the virus to certain cell types.

The synthetically enveloped viruses hereof do not require specific protein-protein interactions or covalent bonds to retain the outer envelope. As a result, the synthetic envelope is stable but retains the capacity to be shed during an infection step. This is in contrast to, for example, the natural lipid envelope added to the MV virus to form the EV form. In this case the outer membrane requires specific protein interactions and is still highly unstable. In that regard, it has traditionally been impossible to purify and store the EV form of vaccinia because the outer envelope is too unstable. Using the synthetic envelopes hereof, a composition may be stored for at least some period (freeze/thawed, etc). Nonoptimized studies have shown that the compositions may be stored for at least one month with one freeze/thaw cycle.

The present devices, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 1A illustrates an idealized, schematic representation of the formation of a representative embodiment of enveloping a virus wherein the envelope is a lipid bilayer.

FIG. 1B illustrates representative examples of cleavable groups for use in the envelopes hereof.

FIG. 1C illustrates representative examples of lipids for use in the envelopes hereof.

FIG. 1D illustrates viral gene expression and anti-tumor effects after intravenous delivery in naïve or immunized mice, wherein BALB/c mice were either immunized (IP injection of 1e6 plaque-forming units or PFU of wild type vaccinia strain WR) or not, and 28 days later implanted subcutaneously with 4T1 tumors.

FIG. 1E illustrates viral gene expression and anti-tumor effects after intratumoral delivery in naïve or immunized mice, wherein BALB/c mice were either immunized (intraperitoneal or IP injection of 1e6 PFU of wild type vaccinia Western Reserve strain or WR) or not, and 28 days later implanted subcutaneously with 4T1 tumors.

FIG. 2A illustrates an electron microscope photomicrograph confirming viral encapsulation, wherein virus (WR.TK-Luc+) was enveloped with a lipid layer including PEG-FTS-H, pH-sensitive lipid and encapsulation was confirmed by electron microscopy (EM) and zetasizer.

FIG. 2B illustrates another electron microscope photomicrograph confirming viral encapsulation with a lipid that was not pH sensitive.

FIG. 2C illustrates a graph of size distribution by intensity for the virus prior to enveloping.

FIG. 2D illustrates a graph of size distribution by intensity for virus (WR.TK-Luc+) enveloped with a lipid layer including PEG-FTS-H lipid.

FIG. 3 illustrates in vitro comparison of different coating formulations, wherein Virus (WR.TK-Luc+) was enveloped with either PEG-FTS or DSPE-PEG containing lipid layers, or left uncoated.

FIG. 4A illustrates in vivo delivery of naked and enveloped virus, wherein athymic nu/nu mice were implanted with HCT 116 tumors and once palpable, high dose vaccinia immune globulin or VIG was delivered via IP injection 24 h prior to IV delivery of naked or enveloped WR.TK-Luc+ (1e8 PFU/mouse, n=4/group), and viral gene expression was measured as bioluminescence 24 h later.

FIG. 4B illustrates viral expression as bioluminescence for in vivo delivery of naked and enveloped virus.

FIG. 6A illustrates the effects of repeat delivery in tumor-bearing mice on tumor volume (via caliper measurement), wherein mice (BALB/c bearing subcutaneous Renca tumors) were treated with an IV dose of WR.TK-.GFP+ and then, with three days between treatments, with WR.TK-Luc+.

FIG. 6B illustrates the effects of repeat delivery in tumor-bearing mice on tumor volume (via caliper measurement), wherein mice (BALB/c bearing subcutaneous Renca tumors) were treated with an IV dose of WR.TK-.GFP+ and then, with 17 days between treatments, with WR.TK-Luc+.

DETAILED DESCRIPTION

Figure 1A:
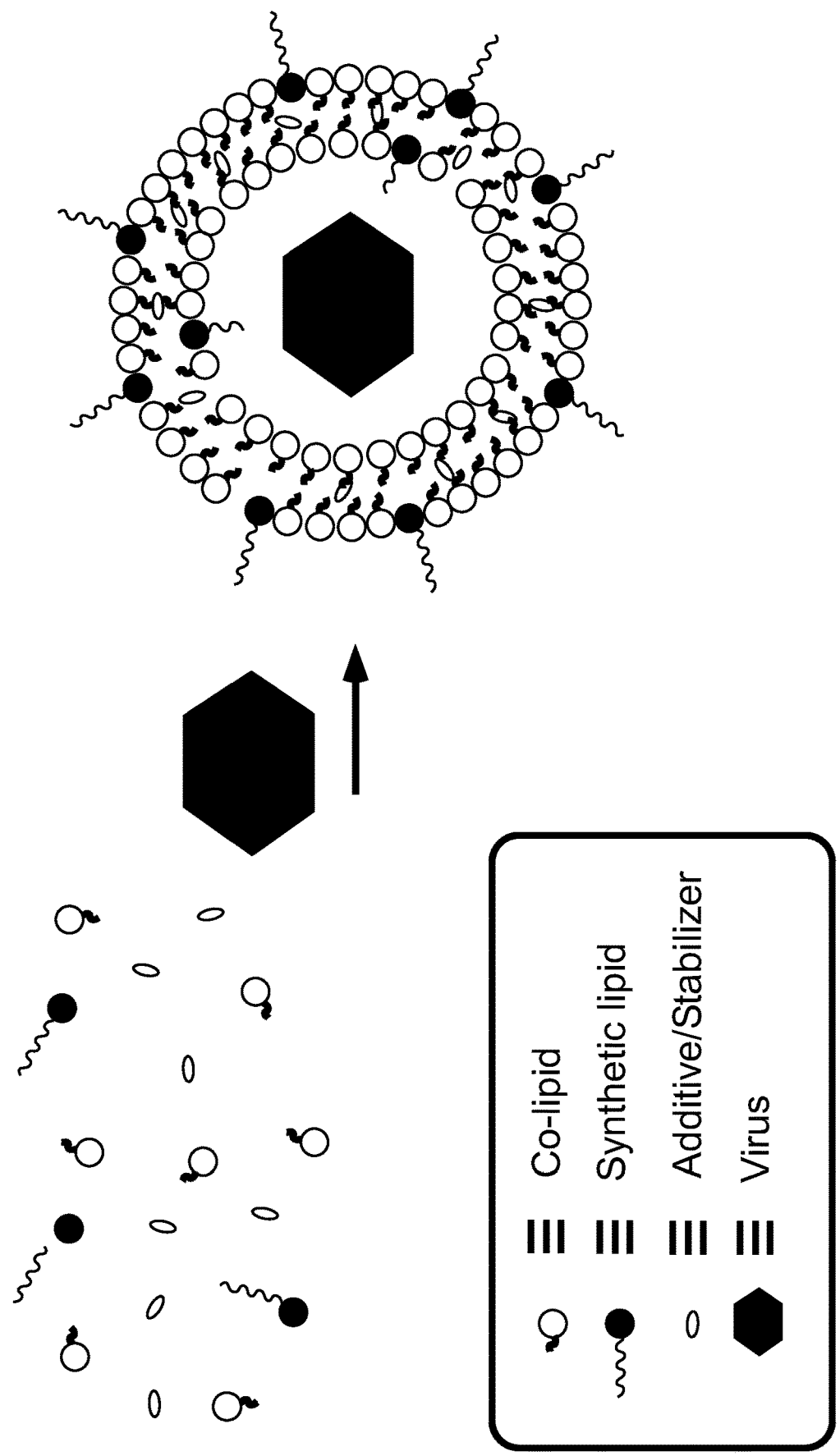
FIG. 1F illustrates tumor volume as a function of time after intravenous delivery in naïve or immunized mice.
FIG. 1G illustrates tumor volume as a function of time after intratumoral delivery in naïve or immunized mice.
Figure 1B:
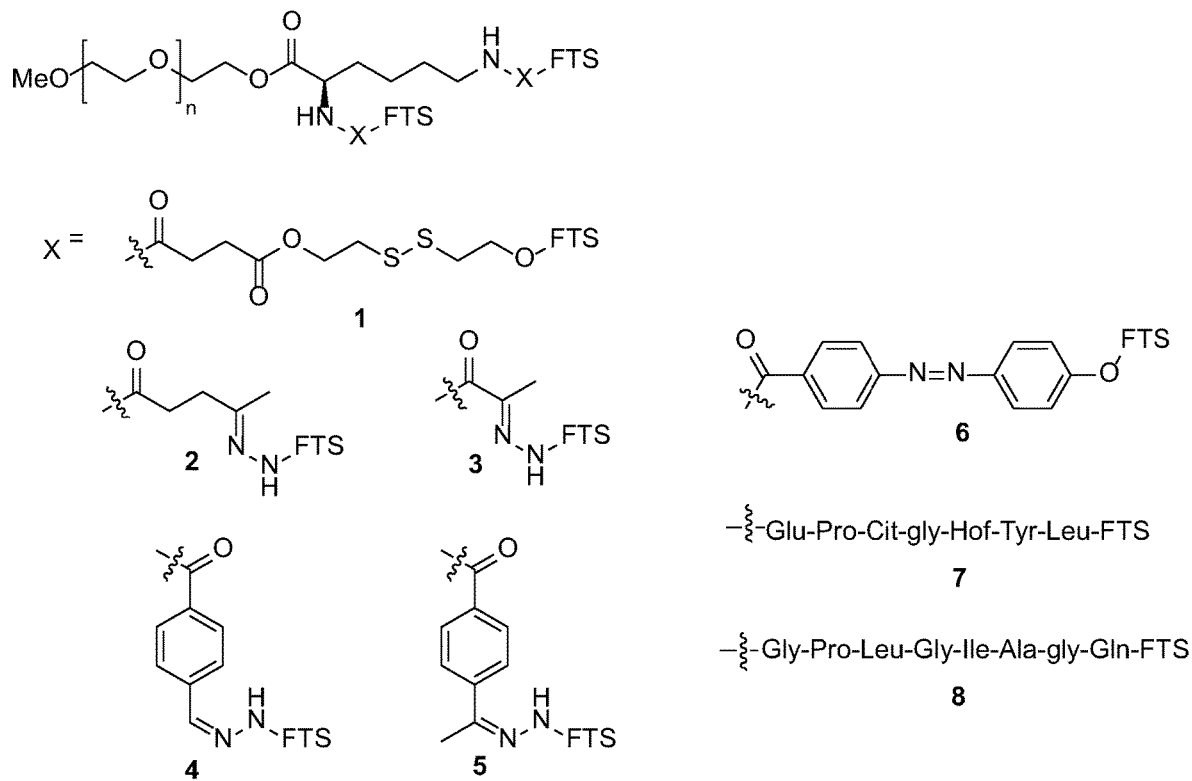
Figure 1C:
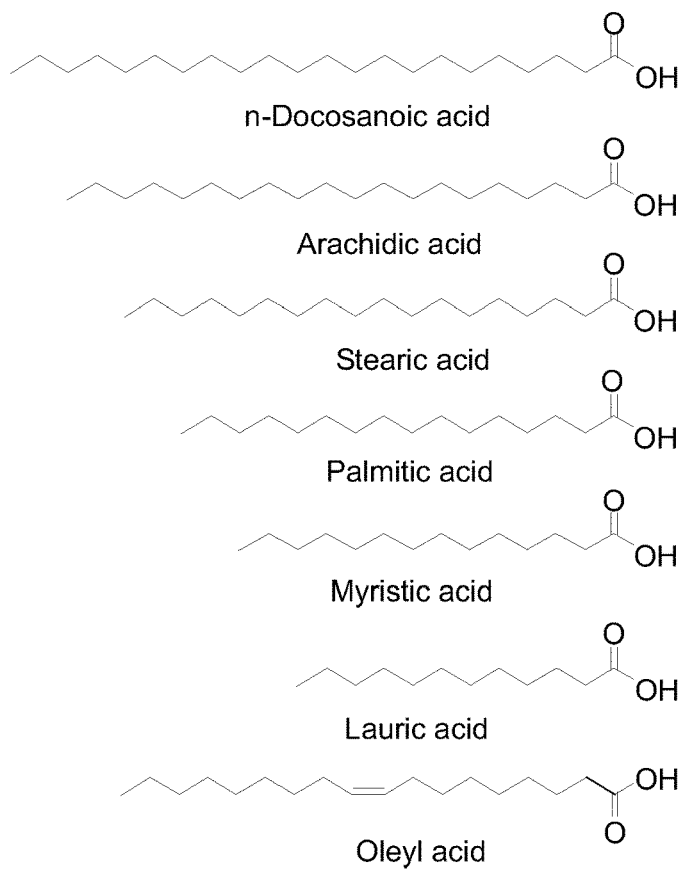
Figure 1D:
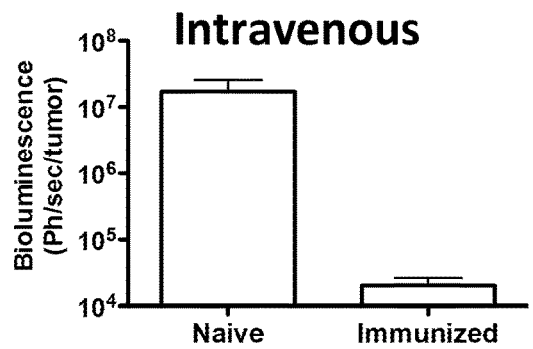
Figure 1E:
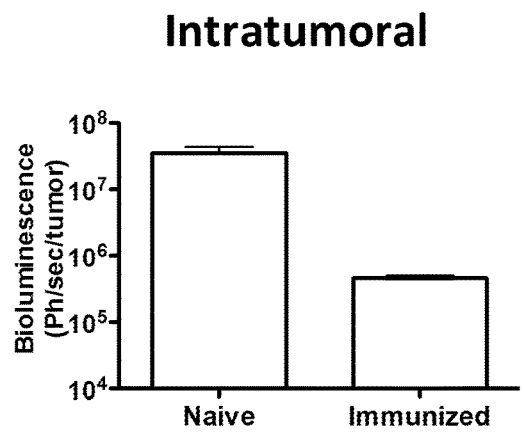
Figure 1F:
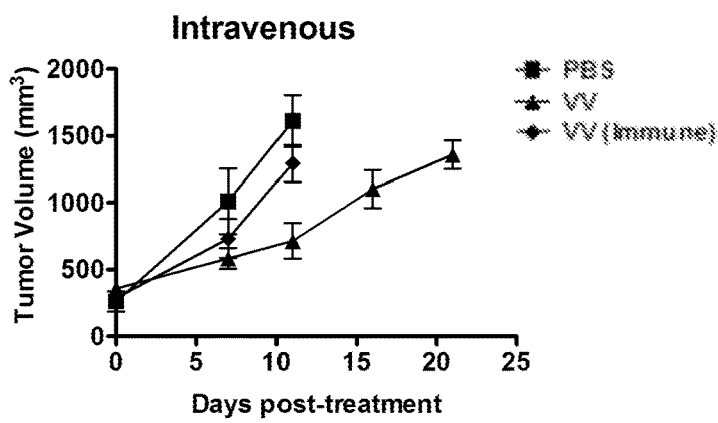
Figure 1G:
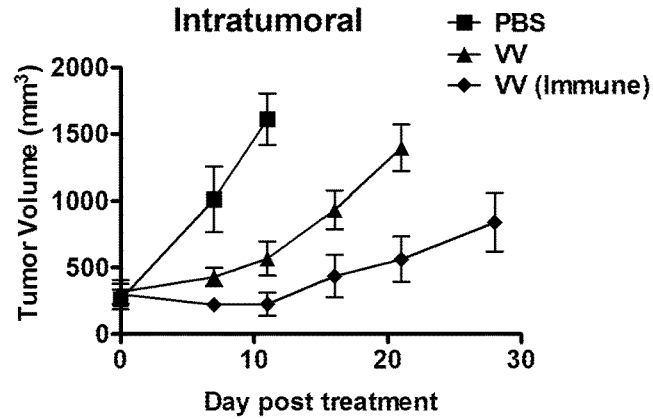
Figure 5A:
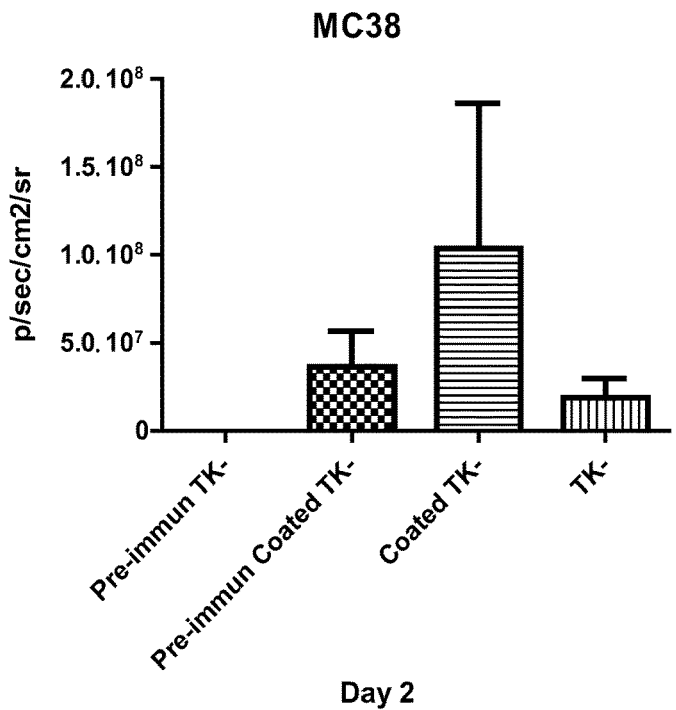
FIG. 5A illustrates viral gene expression measured after 24 h of tumor growth as bioluminescence in fully immunized mice, wherein C57/BL6 mice were immunized (or not) 28 days prior to implantation with MC38 tumor cells; and wherein once tumors were palpable mice were treated with an IV injection of WR.TK-Luc+, naked or enveloped as before.
Figure 5B:
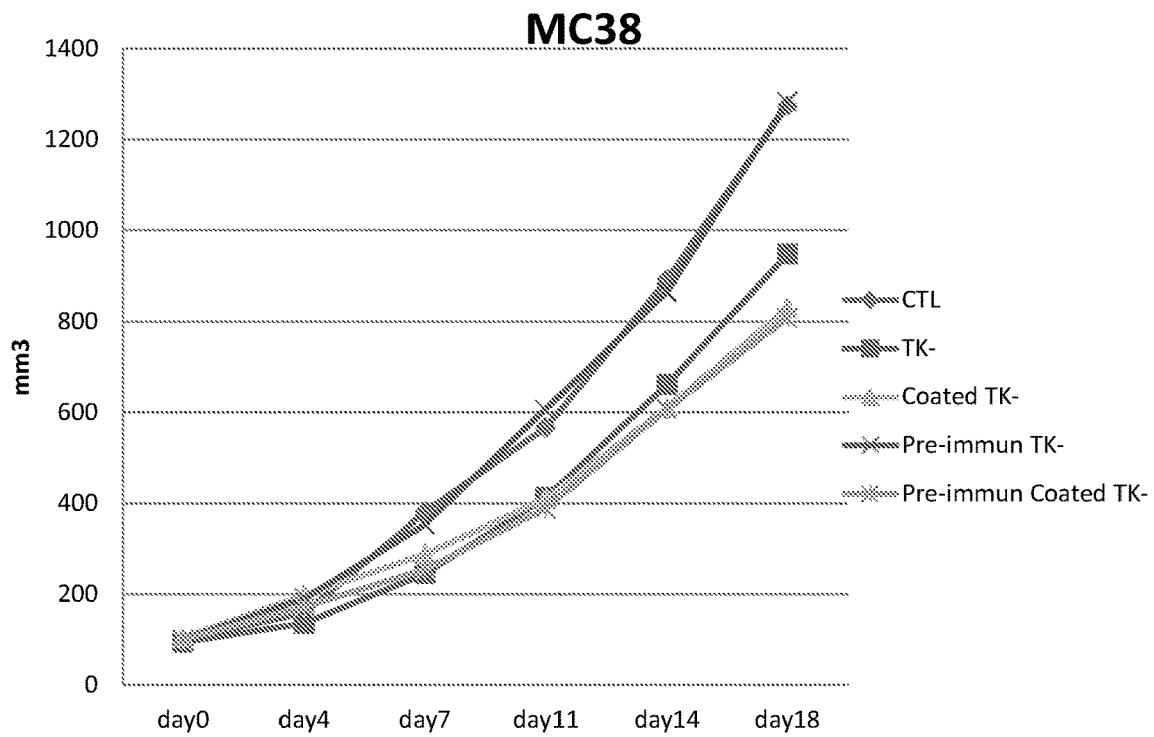
FIG. 5B illustrates anti-tumor effect as measured by tumor volume (via caliper measurement) over time in the studies of FIG. 5A.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a virus" includes a plurality of such viruses and equivalents thereof known to those skilled in the art, and so forth, and reference to "the virus" is a reference to one or more such viruses and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "virus", "virion" and "viral particle" are used interchangeably herein. Often, the term "virus" is used collectively. A virus is a submicroscopic infectious agent that is unable to grow or reproduce outside a host cell. A virus includes genetic material (DNA or RNA) within a protective protein coat known as a capsid. Capsid shapes vary from simple helical and icoshedral (polyhedral or near-spherical) forms, to more complex structures with tails or an envelope. Viruses used in the systems, methods and compositions hereof may be natural viruses or engineered/modified viruses.

As used herein, the term "polymer" refers to a chemical compound that is made of a plurality of small molecules or monomers that are arranged in a repeating structure to form a larger molecule. Polymers may occur naturally or be formed synthetically. The use of the term "polymer" encompasses homopolymers as well as copolymers. The term "copolymer" is used herein to include any polymer having two or more different monomers. Copolymers may, for example, include alternating copolymers, periodic copolymers, statistical copolymers, random copolymers, block copolymers, graft copolymers etc. Examples of polymers include, for example, polyalkylene oxides.

As used herein, the term "lipid" refers to a group of molecules that include, for example, fats, fatty acids, waxes, sterols, fat-soluble vitamins (such as vitamins A, D, E, and K), monoglycerides, diglycerides, triglycerides, phospholipids, and others. Lipids are related by their solubility in nonpolar organic solvents and general insolubility in water. Phospholipids are a class of lipids that, for example, form a major component of all cell membranes. Phospholipids may form lipid bilayers as a result of their amphiphilic characteristic. A phospholipid molecule may, for example, include two hydrophobic fatty acid "tails" and a hydrophilic "head" joined together by a glycerol molecule.

Efforts to protect oncolytic viruses with lipid envelopes or polymer coatings may be successful at detargeting the viral vectors from normal tissues, such as the liver, and even evading anti-viral immunity to some extent. However this benefit has traditionally come at the cost of a significant loss of viral infectivity of the tumor (with recovery of around 5% of the virus typical). Although cationic polymers may exhibit better retention of viral infectivity than other encapsulation materials, cationic polymer exhibit toxicity issues. Strategies of viral encapsulation hereof overcome many of the limitations associated with existing methodologies and may provide a powerful means to deliver virus to tumor targets, even in the face of pre-existing anti-viral immunity. Viral encapsulation systems, methods and compositions hereof are discussed in connection with representative examples of oncolytic viruses. However, one skilled in the art will recognize that such viral encapsulation systems, methods and compositions are applicable in any viral therapy.

As described above, strategies of viral encapsulation hereof overcome many of the limitations associated with existing methodologies and provide a powerful mechanism to deliver virus to tumor targets, even in the face of pre-existing anti-viral immunity. In a number of embodiments, viruses, virions or viral particles (collectively, viruses) are enveloped or encapsulated in a synthetic envelope formed from a composition including a hydrophobic/lipid domain and a hydrophilic domain linked to the hydrophobic/lipid domain. The hydrophilic domain may, for example, be separable from the hydrophobic/lipid domain under physiological conditions present in a target region or region of interest (that is, a region targeted for treatment). There may be more than one region of interest distributed throughout the body (for example, in the case of disseminated cancerous tumors). In a number of embodiments, the synthetically enveloped virus is a synthetic version of a naturally occurring and infectious enveloped viral form of the virus. In such embodiments, infection of target cells may, for example, be optimized.

Synthetic envelops hereof may, for example, include a synthetic lipid conjugate including a hydrophobic/lipid domain linked or conjugated to a hydrophilic domain (for example, a hydrophilic polymer domain including, for example, a polyethylene oxide such as polyethylene glycol) via a linker which is labile or cleavable under physiological conditions present in the region of interest. In a number of embodiments, the linker is a pH sensitive linker. Such a modified virus, is stable in blood and can evade anti-viral antibodies, thereby allowing systemic delivery to, for example, an acidic tumor environment. Once, in the tumor, the hydrophilic domain is de-grafted via cleavage of the pH-sensitive linker, destabilizing the synthetic virus envelope and leading to release of the infectious synthetically enveloped virus. In a number of representative studies hereof, such a synthetically enveloped virus displayed enhanced systemic delivery and therapeutic effects in mouse models, even in the face of pre-existing anti-viral immunity or during repeated systemic delivery.

FIG. 1A illustrates an idealized schematic diagram of a representative embodiment of a synthetic lipid envelope hereof encompassing a virus. In the illustrated embodiment, the envelope forms a closed lipid bilayer. A bilayer is a preferred structure of lipids in aqueous solutions. In a number of embodiments hereof, the synthetic lipid conjugates hereof are combined with one or more co-lipids in forming the synthetic envelope. The colipid(s) may, for example, form the major lipid component of the envelop/bi-layer. In a number of embodiments, co-lipids in the form of phospholipids are the major component in the envelope/lipid bilayer. Increasing the amounts of synthetic lipid conjugates helps to decrease the interaction with blood components and the rapid clearance from the circulation. However, incorporation of too much such lipid conjugates may compromise the stability of the lipid bilayer. In a number of embodiments hereof, no greater than 20 mol % of hydrophilic compound-lipid conjugates are incorporated. The hydrophilic compound-lipid conjugates may, for example, be present in the range of 5 to 20 mol %. Co-lipids may, for example, be present in the range of 40 to 95 mol %. Additives such as DOPE or cholesterol may, for example, be present in the range of 0 to 40 or 10 to 40 mole %. Various phospholipids maybe be used as co-lipids herein including, but not limited to, natural and synthetic phosphatidylcholines or PC (for example, L-α-phosphatidylcholine), phosphatidylethanolamine or PE (for example, L-α-phosphatidylethanolamine) and phosphatidylinositol or PI (for example, L-α-phosphatidylinositol). Natural phosphatidylcholines include, for example, egg PC, heart PC, soy PC, brain PC and liver PC. Synthetic phosphatidylcholines include, for example, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC). Natural phosphatidylethanolamines include, for example, egg PE, heart PE, soy PE, brain PE, liver PE. Synthetic phosphatidylethanolamines include, for example, 1,2-dilauroyl-sn-glycero-3-phosphoethanolamine (DLPE), 1,2-dimyristoyl-sn-glycero-3-phosphoethanolamine (DMPE), 1,2-dihexadecanoyl-sn-glycero-3-phosphoethanolamine (DPPE), and 1,2-distearoyl-sn-glycero-3-phosphoethanolamine (DSPE). Natural phosphatidylinositols include, for example, liver PI, soy PI, brain PI. Synthetic phosphatidylinositols include, for example, 1,2-dihexadecanoyl-sn-glycero-3-phospho-(1'-myo-inositol) DPPI, 1,2-dioleoyl-sn-glycero-3-phospho-(1'-myo-inositol) DOPI, and 1,2-distearoyl-sn-glycero-3-phospho-(1'-myo-inositol) (DSPI). The efficiency of the enveloped virus may, for example, further tuned by readily optimizing the lipid composition of the envelope/bilayer for a particular envelope, virus and/or application.

The synthetic envelopes hereof may, for example, include one or more further substituents which are references generally as additives in FIG. 1A. Such additives may, for example, function to modulate the stability of the synthetic envelope. Cholesterol, for example, may assist in stabilizing a lipid bilayer. On the other hand, 1,2-dioleoyl-sn-glycero-3-phosphoethanolamine (DOPE) is a fusogenic lipid. Inclusion of DOPE may decrease the lipid stability and facilitate the release of virus from endosome following intracellular delivery. Various other additive may be similarly used to adjust or tune the properties of the compositions or formulations hereof.

The identity and concentration of various additives is also subject to optimization for a particular envelope, virus and/or application via known activities and/or routine experimentation. In the case of a stabilizing component such as cholesterol, for example, while a stable lipid bilayer might be desirable, an overly stable bilayer may negatively affect the un-coating of virus following internalization into cells.

As discussed above, synthetic lipid envelopes (including synthetic lipid conjugates hereof) assist in prevent nonspecific interaction of viruses with serum proteins, which is important for a prolonged circulation time in the blood and effective targeting to the tumors. Further, the labile or cleavable linker in the synthetic lipid conjugates hereof provides for controlled shedding of the synthetic envelope.

In a number of studies, representative vaccinia viruses were encapsulated or enveloped with synthetic envelopes hereof. The vaccinia virus, which may be the backbone for multiple clinical vectors, can exist in different infectious forms, distinguished by the number of lipid envelopes shrouding the viral core. These forms include the most basic infectious form (Intracellular Mature Virus, IMV or Mature Virus, MV) and a version of the IMV that has an additional host cell derived lipid envelope (the Enveloped virus, EV). The application of an artificial or synthetic hydrophobic/lipid envelope to the IMV form of the virus creates a synthetic version or mimic of the EV form that has naturally evolved multiple routes of cell entry. Unlike a number of artificially enveloped or coated viruses, synthetic EV may retain a more robust capacity to infect tumor cells. In a number of representative embodiments, use of a pH-sensitive linker to attach a hydrophilic domain to the hydrophobic/lipid envelope acts to protect the viral particle while in circulation, but is cleaved from the envelope encompassing the viral particle once in the acidic tumor environment or after entry into the endosomal pathway. In the case of target regions or regions of interest other than acidic tumor environments, the cleavable bond may be responsive or sensitive to other microenvironments present within the regions of interest (for example, reduction/oxidation potential, hypoxia and matrix metalloproteinase-9) (see FIG. 1C for representative examples). The combination of synthetically mimicking a naturally existing viral form and incorporation of advanced lipid technology is present in a number of embodiments hereof. However, the systems, methods and compositions hereof are applicable to viral therapies generally and need not mimic a naturally existing enveloped viral form.

As described above, the incorporation of a vaccinia backbone in a number of embodiment hereof allows the addition of a synthetic lipid envelope to a form of the virus (the IMV) resulting in the production of a synthetic version or mimic of a naturally evolved form of the virus (EV). In this way, a synthetic version of a naturally occurring virus is formed and the viruses natural cell entry pathways are not disrupted. Indeed, even when a 'standard' lipid envelope (that is, a lipid envelop not including a synthetic lipid conjugate hereof) is used, recovery of the vaccinia virus is 10 times better than reported in the previous models.

The hydrophilic compounds used in forming the hydrophilic domains of the synthetic lipid conjugates hereof may, for example, include at least one hydrophilic oligomer or at least one hydrophilic polymer. The hydrophilic oligomer or the hydrophilic polymer may, for example, be selected from the group consisting of a polyalkylene oxide, a polyvinylalcohol, a polyacrylic acid, a polyacrylamide, a polyoxazoline, a polysaccharide and a polypeptide. In a number of embodiment, the at least one hydrophilic compound is a polyalkylene oxide. In a number of representative embodiments hereof, the polyalkylene oxide is a polyethylene glycol (PEG). In a number of embodiments, the hydrophilic compound (for example, PEG) has a molecular weight of at least 1 KDa (for example, in the range of approximately 1 KDa to 10 KDa). In a number of embodiments, the hydrophilic domain has a molecular weight in the range of approximately 1 KDa to 5 KDa. The hydrophilic domain(s) of the synthetic lipid conjugates hereof, for example, include a single or multiple chains.

Many different hydrophobic compounds may be used in the hydrophobic domains of the synthetic lipid conjugates hereof. Representative example of such hydrophobic compounds are provided in FIG. 1B. The hydrophobic domain(s) of the synthetic lipid conjugates hereof, for example, include a single or multiple chains.

In a number of representative embodiments, synthetic lipid conjugate compositions used to create the envelope included farnesylthiosalicylic acid (FTS) or a derivative of farnesylthiosalicylic acid conjugated to PEG with a pH sensitive and tunable hydrazine linker. The use of such materials provides several advantages. The FTS or FTS derivative may, for example, be a biologically active derivative of farnesylthiosalicylic acid including, for example, be S-trans, trans-farnesylthiosalicylic acid, S-trans, trans-farnesylthiosalicylic acid amide, S-trans, trans-farnesylthiosalicylic acid methylamide (FTS-MA) or S-trans, trans-farnesylthiosalicylic acid dimethylamide (FTS-DMA). Other biologically active farnesylthiosalicylic acid derivatives are also suitable for use herein. In that regard, FTS itself has antitumor activity (as a ras inhibitor) that can combine with the different mechanisms of anti-tumor activity brought through the viral payload. Moreover, the cleavage of PEG-FTS-H in response to pH changes may be readily fine-tuned by, for example, choosing various lengths of the carbon chain or appropriate electron-withdrawing/contributing groups close to the hydrazone linker. This methodology provides control over the rate of PEG degrafting following the delivery of enveloped viruses to the tumor tissues.

S-trans, trans-farnesylthiosalicylic acid (FTS), which is shown below, 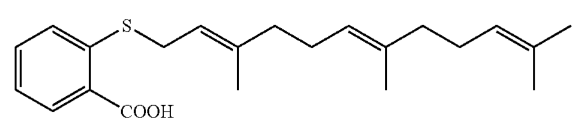 [SMILES: CC(C)=CCC/C(C)=C/CC/C(C)=C/CSc1ccccc1C(=O)O] is a synthetic farnesylcysteine mimetic that acts as a potent and especially nontoxic Ras antagonist. Constitutively active Ras caused by mutation in the Ras family of proto-oncogenes is present in one-third of human cancers, with the highest incidence of mutational activation of Ras being detected in pancreatic (90%) and colon (50%) cancers. Ras is also activated in cancer cells by other mechanisms. In particular, hyperactivation of the epidermal growth factor receptor (EGFR) tyrosine kinase activity causes persistent activation of Ras and Ras-mediated signaling. The activated form of Ras constitutively activates its downstream effectors, contributing to cell transformation. FTS can inhibit both oncogenically activated Ras and growth factor receptor-mediated Ras activation, resulting in the inhibition of Ras-dependent tumor growth. FTS can inhibit Ras transforming activity and reverse the transformed phenotype of Ras-transformed fibroblasts. FTS has demonstrated significant reduction of Ras levels in a wide array of established cancer models and inhibition of tumor growth in animals with no adverse toxicity. One major mechanism involves affecting membrane interaction of Ras by competing with Ras for binding to Ras-escort proteins, facilitating its degradation, and thus disrupting Ras protein to signal in the plasma membrane. In addition to its antitumor activity, FTS also exhibits anti-inflammatory activity. Conjugation of FTS or an FTS derivative having, for example, the formula:

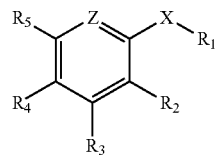

Wherein $R_1$, $R_2$, $R_3$, $R_4$, $R_5$, X and Z are defined as describe above with one or more hydrophilic compounds (for example, hydrophilic oligomers or polymers such a polyethylene glycol or PEG) may provide antitumor or Ras antoginst activity independent of and synergistic with the viral therapy.

In a number of representative embodiments hereof, pH-sensitive compositions were formed by conjugating a hydrophilic PEG segment to one or more hydrophobic FTS-hydrazide or FTS-H segments with a cleavable hydrazine linker. The use of a representative PEG-(FTS-H)$_2$ (pH sensitive PEG linker) on the lipid envelope resulted in 100% recovery of infectious vaccinia virus in tissue culture, which has not been previously achieved with other encapsulation technologies. The envelope also provides protection against neutralizing antibody, confirming that the envelope is active and functioning to protect the virus as expected.

Further, in vivo applications in mouse tumor models showed that use of enveloped vaccinia viruses hereof not only reduced viral uptake in non-tumor tissues, but actually resulted in improved/increased delivery to the tumor (relative to naked virus in naïve mice). This is the first time of which the inventors are aware that an encapsulation technology actually enhanced delivery to the tumor.

Delivery of an active virus to a tumor or other region of interest is only possible in the face of anti-viral immunity when the viral vectors were enveloped. In a number of embodiments hereof, enveloped virus delivered systemically in fully immunized mice actually displayed increased viral gene expression from the tumor compared to naked virus delivered in naïve (non-immunized) mice. This is a dramatic improvement on any previously reported approach.

Enhanced delivery of the enveloped viruses hereof also manifested itself in enhanced therapeutic activity in several manners. In that regard, enveloped virus displayed enhanced therapeutic effects relative to naked virus when either was delivered systemically in naïve animals. Indeed, the therapeutic benefit achieved when enveloped virus was delivered systemically in fully immunized mice was even better than for naked virus in naïve, non-immunized mice (whereas naked virus in immunized mice had no therapeutic effect). Moreover, when repeat cycles of treatment were applied in a naïve, tumor-bearing animal, additional cycles had no additional therapeutic benefit for naked virus, but provided significant further benefit when enveloped virus was used. Such data indicate that systems, methods and compositions hereof provide a significant advance over other reported approaches.

In a number of representative experiments, the capacity for delivery of naked virus (determined by luciferase transgene expression within the tumor) and therapeutic outcome after delivery via different routes and with or without pre-existing immunity were explored. BALB/c mice were either immunized (IP injection of 1e6 PFU of wild type vaccinia strain WR) or not, and 28 days later implanted subcutaneously with 4T1 tumors. Once large tumors were formed (that is tumors having a volume of approximately 300-400 mm$^3$), mice were treated with either intravenous (tail vein) or intratumoral injection of a model oncolytic vaccinia strain (1e8 PFU of strain WR with a deletion in the thymidine kinase, TK gene and expressing luciferase as a reporter; all three vaccinia strains currently undergoing clinical testing contain a deletion in the TK gene.) Subsequent tumor volume and viral gene expression from within the tumor were followed as set forth in FIG. 1D through 1G.

For naive mice, there were no significant differences in anti-tumor effects between intravenous or intratumoral delivery. Although viral gene expression appeared slightly lower after intravenous delivery this was not significant (p=0.1). In previously immunized mice, intravenous delivery resulted in almost no viral gene expression in the tumor (background levels of bioluminescence were determined at 1e4 ph/sec/tumor). Unsurprisingly, this correlated with no therapeutic benefit. Intratumoral delivery in previously immunized mice did produce detectable viral gene expression from the tumor, but this was still >50-fold less than viral gene expression for naïve mice. Without limitation to any mechanism, the reduction may largely be a result of anti-viral T-cell based immunity targeting infected tumor cells, as imaging was taken 24 h post delivery, and prior to spread of progeny virus. Notwithstanding the significant reduction in viral gene expression, there is actually a significant increase in therapeutic effect. The increase in therapeutic effect may, for example, be mediated by the immunotherapeutic effect of the OV therapy (as oncolytic effects are reduced). Those results both reinforce the hypothesis that the most effective OV therapies act primarily as immunotherapies, but also highlight the potential importance of successful OV delivery to the tumor in pre-immunized patients.

Lipid-hydrophilic polymer conjugates or composition such as lipid-alkylene oxide conjugates, may be used in forming micelles as carriers for delivery of small-molecule chemotherapies to tumor targets. Incorporation of an additional labile linkage such as a reduction sensitive (for example, disulfide) linkage into a lipid-hydrophilic polymer conjugate such a conjugate of 5 kDa PEG and two farnesylthiosalicylic acid groups (PEG5k-FTS$_2$) led to an increase in tumor cell growth inhibitory effect and a further improvement in its performance in delivery of, for example, paclitaxel (PTX) to tumor cells in vitro and in vivo. See, for example, U.S Patent Application Publication Nos. 2015/0306034 and 2015/0231271, the disclosures of which are incorporated herein by reference. Synthetic techniques thereof may be adapted for use in the synthesizing lipid-hydrophilic conjugates hereof.

As described above, in a number of representative embodiments hereof, pH-sensitive compositions were formed by conjugating a hydrophilic PEG segment to one or more hydrophobic FTS-H segments with a cleavable linker such as a hydrazine linker. Once again, the stability of the hydrazine linker may be readily modulated by choosing different carbon chain lengths or appropriate electron-withdrawing/contributing groups around the hydrazine linker. It is thereby possible to develop a linker that is cleaved when exposed to the acidic pH found in, for example, a tumor microenvironment.

In a representative methodology, lipid films containing DMPC: Cholesterol: PEG5K-FTS-H2 at a 2:1:0.1 ratio were mixed with the Mature Virus (MV form of oncolytic vaccinia WR.TK-.Luc+) in a PBS buffer and sonicated to create lipid enveloped viral particles. The viral preparation methods produce virus containing >98% MV, which contains a single outer envelope (as opposed to the Enveloped virus, EV form that has an additional lipid envelope). The synthetically enveloped MV were examined by EM to confirm that close to 100% of the viral particles were enveloped, and that viral particles were enveloped as single particles (with no clumps or doublets) (see FIGS. 2A and 2B). In addition, electron microscopy was used to confirm the integrity of the envelopes. FIGS. 2C and 2D illustrates size distribution by intensity for virus prior to enveloping and for virus (WR.TK-Luc+) enveloped with a lipid layer including PEG-FTS-H lipid, respectively.

In a number of initial in vitro experiments, MV vaccinia virus was again encapsulated with a PEGSK-FTS-$H_2$ containing envelope. The experimental results were compared to naked virus and a more standard lipid encapsulation technology (that is, a lipid encapsulation technology other than the those including the synthetic lipid conjugates hereof and, thus, not including a cleavable hydrophilic domain) DMPC: Cholesterol: DSPE-PEG2K at a 2:1:0.1 M ratio) so that the advantages of encapsulating the MV form of vaccinia and the use of a pH-sensitive envelope encapsulation hereof could be explored.

Naked virus, PEG-FTS and DSPE-PEG enveloped virus were mixed with high doses of VIG (vaccinia immunoglobulin) or PBS for 30 minutes before addition to a fresh cell layer (of HeLa cells). The PEG-FTS enveloped virus groups were additionally treated at neutral or lower pH prior to addition to the cell layer.

FIG. 3 illustrates in vitro comparison of different coating formulations, wherein Virus (WR.TK-Luc+) was enveloped with either PEG-FTS or DSPE-PEG containing lipid layers, or left uncoated. Virus was then either mixed with high dose VIG for 30 minutes, or left without antibody. The PEG-FTS enveloped virus then additionally had HCl added to lower the pH. Virus was then added to a HeLa cell layer, left for 24 h for infection and gene expression to occur, before bioluminescence was read. It was determined from FIG. 3 that use of a DSPE-PEG envelope (without VIG) resulted in about 50% recovery relative to naked virus. This result is a significant improvement over any similar reported technologies with other viral backbones, where recovery of 1-5% is typical. Such results may are evidence of an advantage of encapsulating the MV form of vaccinia, to create a synthetic version of the EV, so retaining natural viral infection pathways.

However, when PEG-FTS was incorporated as a viral envelope, 100% recovery was achieved (after exposure to lower pH to degraft PEG) relative to naked virus. It is therefore apparent that combining vaccinia MV form for encapsulation with pH-sensitive PEG degrafting technology resulted in complete recovery of the virus. Whereas exposure to VIG completely neutralized the naked virus, PEG-FTS coated virus was protected and around 50% infectious virus was recovered. This result was obtained even though degrafting of PEG (through lowering of pH) occurred prior to layering of the particles (plus VIG) onto the cell layer for the infection step.

In a subsequent set of representative experiments, naked or PEG-FTS enveloped virus were delivered intravenously (tail vein, 1e8 pfu/mouse, n=4 per group) to subcutaneous HCT 116 tumor-bearing athymic nude mice (see FIGS. 4A and 4B). In some groups, animal had previously received an intraperitoineal injection of VIG. In this way, it was possible to examine delivery in the face of neutralizing antibody without dealing with loss of tumor signal as a result of the CTL response targeting infected tumor cells.

Unexpectedly, when synthetically enveloped virus (eVV) hereof was compared to naked virus (VV) in the absence of VIG, the enveloped virus displayed significantly enhanced ($p=0.009$) viral gene expression from the tumor, indicating more efficient delivery. When similar comparisons were made for a region of interest drawn over the upper body of the mouse (including natural viral targets such as liver, spleen and lungs, but not the tumor), eVV displayed a 5-fold reduction in signal from normal tissues. This reduction is typical for successfully detargeted viral particles, but this usually occurs at the expense of infection of the tumor target. In the case of the enveloped viruses hereof, one actually sees an increase in infection within the tumor.

When VIG was present, naked virus produced no detectable signal from the tumor. However enveloped virus was still capable of producing high levels of tumor signal (although this was reduced around 3-fold relative to enveloped virus delivery in naïve mice).

In another set of representative experiments, delivery and anti-tumor effects were compared in naïve and fully immunized mice. Immunocompetent animals were initially vaccinated with wild type vaccinia (strain WR, IP 1e6 PFU) or left unvaccinated as controls. Vaccinated animals were left for 28 days to ensure virus was cleared and that the adaptive response had entered the memory phase, so as not to effect tumor implantation. Mice were then implanted with MC38 tumors subcutaneously. Once tumors became palpable, mice were treated with a single intravenous injection of 1e8 PFU of WR.TK− or enveloped WR.TK− (see FIGS. 5A and 5B).

As observed with the nude mouse model, it was seen that enveloped virus was actually more efficient at infecting the tumor after systemic delivery in naïve mice relative to naked virus. As expected, no viral gene expression was detected in the tumor after systemic delivery in previously immunized animals. Remarkably, enveloped virus produced greater viral gene expression in the tumor after delivery in immunized mice than naked virus achieved after delivery to naïve mice, this is despite the expected anti-viral effects of the CTL response after infection of cells in the tumor.

The enhanced viral gene expression of the enveloped viruses hereof also translated into enhanced therapeutic activity. Whereas naked virus produced modest delays in tumor growth in this model in naïve mice, it had no effect when delivered to previously immunized mice. Enveloped virus hereof produced significantly enhanced therapeutic effects (relative to naked virus in naïve mice) whether it was delivered in naïve or pre-immunized mice. The enveloped viruses hereof may actually enhance anti-tumor effects relative to naked virus delivered in naïve mice, even when the enveloped virus hereof is delivered systemically in fully immunized animals.

To more accurately model a clinical situation, where a patient may not have been previously exposed to the virus, or may have been vaccinated decades earlier with only limited immunity remaining, experiments were performed to repeat delivery of enveloped or naked virus to tumor bearing mice. Such experiments are complicated by the fact that most syngeneic tumors are highly aggressive and the time frame between tumors becoming palpable and the need to sacrifice the animal is often only 2-3 weeks, about the same time as needed to raise a robust antibody response.

In a number of experiments, BALB/c mice were implanted subcutaneously with RENCA tumors and then treated once the tumors became palpable via the tail vein with 1e8 pfu of either naked or enveloped virus. After a gap of either 3 days or 14 days a second round of the same therapy was delivered. Tumor burden was followed over time. It was seen in FIGS. 6A and 6B that whereas repeat injections of naked virus provided no additional therapeutic benefit relative to a single intravenous injection (single injection tumor volume was 1720 mm³ at day 17 when imaging was taken), enveloped virus produced significant additional therapeutic benefit after repeat cycles of systemic delivery.

Figure 7:
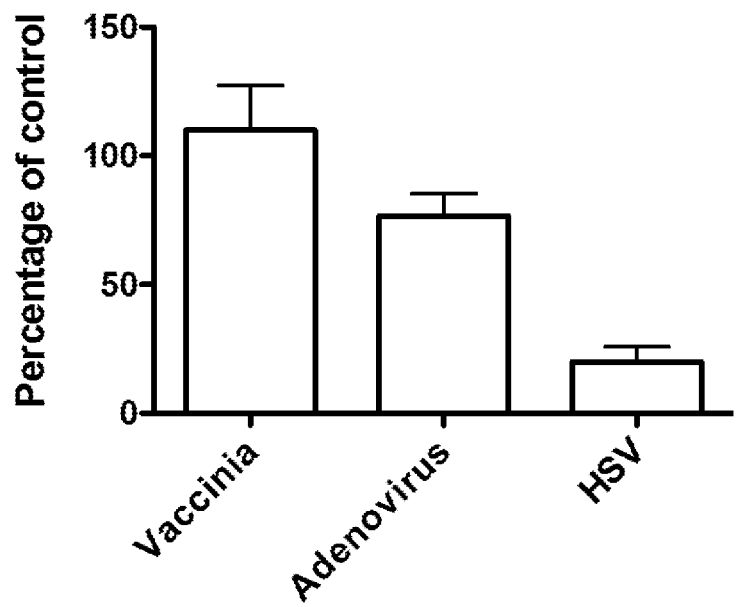
FIG. 7 illustrates percent infection rate of several types of viruses enveloped or encapsulated under the methods hereof as compared to such viruses without the envelopes hereof.

FIG. 7 illustrates percent infection rate of several types of viruses enveloped or encapsulated under the methods hereof as compared to such viruses without the envelopes hereof as controls. Improved results are obtained for representative viruses such as adenovirus (Ad) and HSV. These results indicate that other viral backbones (including both lipid and protein enveloped viruses) can be encapsulated within the synthetic lipid envelopes as described herein while retaining infectious capacity. The retained infections capacity is greater than that reported for previously described technologies (including, approaches to attach PEG to the viral surface to enhance systemic circulation and/or to detarget virus from uptake in non-target tissues (such as the liver)). The infectious capacity, after addition of synthetic envelope for viruses that do not naturally exist in different forms with different numbers of lipid layers (such as Adenovirus or HSV), may be reduced relative to those viruses that do have this capability (such as vaccinia).

The HSV and adenovirus are commonly used as backbones for gene therapy or oncolytic virus therapies. Although there is some loss in infectivity with these viruses, it is relatively small compared to previously described approaches.

Experimental

Cell lines and viral vectors: Tumor cell lines including 4T1 (mouse breast cancer); Renca (mouse renal cancer), HCT 116 (human colorectal cancer) and HeLa (human cervical cancer) were obtained from ATCC. MC38 (mouse colorectal cancer) was obtained from David Bartlett, University of Pittsburgh. Cells were cultured as recommended. Vaccinia Immunoglobulin (VIG) was a kind gift from CDC.

The vaccinia strain WR.TK-Luc+ contains an insertional mutation in the viral thymidine kinase (TK) gene, containing the luciferase transgene under control of the pSE/L promoter, and has been described previously. Virus was amplified in HeLa cells, lysed by freeze/thaw and purified by ultracentrifuge banding and tangential flow.

Mice and mouse models. Mice (athymic nu-/nu-, BALB/c and C57/BL6) were obtained from Charles River and were housed with food and water ad libitum. Tumors were formed through subcutaneous implantation of 1e6 mouse tumor cells or 1e7 human tumor cells. Unless otherwise indicated, once tumor became palpable (50-100 mm³) animals were treated with 1e8 PFU of virus or enveloped virus via tail vein injection. Subsequent tumor volume was determined by caliper measurement and viral gene expression determined by bioluminescence imaging (on an IVIS200, Perkin Elmer after IP delivery of D-luciferin substrate (Gold Bio)).

Figure 8:
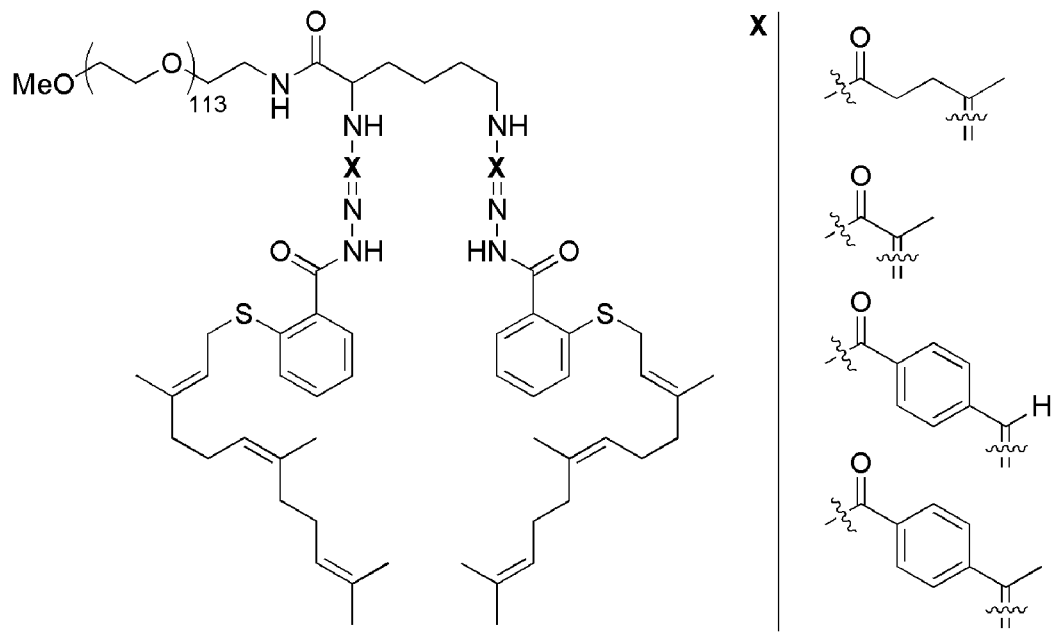
FIG. 8 illustrates the structure of a number of pH-sensitive conjugates hereof.

Synthesis of representative pH sensitive or responsive conjugates. Synthesis of several representative pH sensitive or responsive conjugates suitable for formation of lipidic viral envelopes was carried out. A series of pH-sensitive conjugates, containing two molecules of FTS-H coupled to one molecule of PEG via a hydrazone linker are illustrated in FIG. 8. Conjugates with increasing carbon chain length or electron withdrawing/contributing groups close to the hydrazone linker were studied to demonstrate their tunable pH-sensitivity (see FIG. 8). Synthesis of the four conjugates of FIG. 8 is straightforward, using ketone group on PEGylated molecules to react with FTS-H, which usually completed within 2 hours. Successful synthesis was confirmed via ¹H NMR spectrums and MALDI-TOF of the conjugates.

Viral envelopes. Materials: Dimyristoyl phosphatidylcholine (DMPC), cholesterol (Chol) 1,2-distearoyl-sn-glycero-3-phosphoethanolamine-N-[methoxy(poly ethylene glycol)-2000] (DSPE-PEG2K), PEGSK-FTS-Hydrazide with hydrazine linker (PEGSK-FTS-H2).

Protocol: Dimyristoyl phosphatidylcholine (DMPC), cholesterol, and mPEG-FTS at a 2:1:0.1 molar ratio were dissolved in chloroform in a glass tube. The organic solvent was further removed by nitrogen flow to form a thin film. The film was dried under vacuum for 1 h to remove the remaining solvent. Virus was diluted with PBS, and then added to the tube to hydrate the thin film. The tube with the hydrated film was placed in an ultrasonic water bath (output control setting 4, Sonifer 250) for 30 mins. The encapsulated virus was ready after stabilizing at room temperature for 3 hours.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of modifying a virus for in vivo delivery to a region of interest, comprising:
   forming a synthetic enveloping composition in the form of a lipid layer comprising (i) a lipid conjugate formed by conjugating at least one lipid with at least one hydrophilic compound via a linkage which is cleavable under conditions present in the region of interest and (ii) a co-lipid, wherein the lipid conjugate is present in no greater than 20 mol % in the synthetic enveloping composition, and
   combining the virus with the enveloping composition to encompass the virus within an enveloping structure, wherein cleaving of the linkage under conditions present in the region of interest results in recovery of infectivity of the virus.

2. The method of claim 1 wherein the co-lipid is present in the range of 40 to 95 mol %.

3. The method of claim 1 wherein the co-lipid is a phospholipid.

4. The method of claim 1 wherein the at least one lipid is selected from the group consisting of n-docosanoic acid, arachidic acid, stearic acid, palmitic acid, myristic acid, lauric acid, oleyl acid, vitamin E, embelin, 1-phenyl-2-palmitoylamino-3-morpholino-1-propanol, or a compound having the formula:

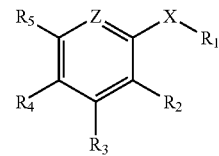

wherein $R_1$ is a farnesyl group, a geranyl group or geranyl-geranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group, or derivative thereof.

5. The method of claim 4 wherein the at least one lipid is selected from the group consisting of S-trans, trans-farnesylthiosalicylic acid, S-trans, trans-farnesylthiosalicylic acid amide, S-trans, trans-farnesylthiosalicylic acid methylamide and S-trans, trans-farnesylthiosalicylic acid dimethylamide.

6. The method of claim 1 wherein a family of the virus is selected from the group consisting of poxvidrae, denoviridae, herpesviridae, picomaviridae, rhabdoviridae, paramyxoviridae, retroviridae, togaviridae or reoviridae.

7. The method of claim 6 wherein the virus is selected from the group consisting of a vaccinia virus, a myxoma virus, an avipox virus, an adenovirus, a herpes simplex virus, coxsackie virus, a vesicular stomatitis virus, a Newcastle disease virus, an adeno-associated virus, a polio virus, a lenti virus, a retrovirus, a reovirus, or a sindbis virus.

8. The method of claim 7 wherein the virus is a mature vaccinia virus.

9. The method of claim 1 wherein the region of interest comprises a tumor and the virus is modified to treat the tumor.

10. The method of claim 1 wherein the at least one hydrophilic compound comprises at least one hydrophilic oligomer or at least one hydrophilic polymer.

11. The method of claim 10 wherein the at least one hydrophilic oligomer or the at least one hydrophilic polymer is selected from the group consisting of a polyalkylene oxide, a polyvinylalcohol, a polyacrylic acid, a polyacrylamide, a polyoxazoline, a polysaccharide and a polypeptide.

12. The method of claim 10 wherein the at least one hydrophilic compound is a polyalkylene oxide.

13. The method of claim 1 wherein the linkage is sensitive to pH.

14. The method of claim 13 wherein the linkage comprises a hydrazine group.

15. A formulation for in vivo delivery to a region of interest, comprising:
a virus;
a synthetic enveloping composition forming a lipid layer encompassing the virus and comprising (i) a lipid conjugate formed by conjugating at least one lipid with at least one hydrophilic compound via a linkage which is cleavable under conditions present in the region of interest and (ii) a co-lipid, wherein the lipid conjugate is present in no greater than 20 mol % in the synthetic enveloping composition.

16. The formulation of claim 15 wherein the co-lipid is present in the range of 40 to 95 mol %.

17. The formulation of claim 16 wherein the co-lipid is a phospholipid.

18. The formulation of claim 15 wherein the at least one lipid is selected from the group consisting of n-docosanoic acid, arachidic acid, stearic acid, palmitic acid, myristic acid, lauric acid, oleyl acid, vitamin E, embelin, 1-phenyl-2-palmitoylamino-3-morpholino-1-propanol, or a compound having the formula:

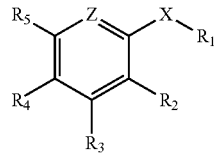

wherein $R_1$ is a farnesyl group, a geranyl group or geranyl-geranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group, or derivative thereof.

19. The formulation of claim 18 wherein the at least one lipid is selected from the group consisting of S-trans, trans-farnesylthiosalicylic acid, S-trans, trans-farnesylthiosalicylic acid amide, S-trans, trans-farnesylthiosalicylic acid methylamide- and S-trans, trans-farnesylthiosalicylic acid dimethylamide.

20. The formulation of claim 15 wherein a family of the virus is selected from the group consisting of poxvidrae, denoviridae, herpesviridae, picornaviridae, rhabdoviridae, paramyxoviridae, retroviridae, togaviridae or reoviridae.

21. The formulation of claim 15 wherein the virus is selected from the group consisting of a vaccinia virus, a myxoma virus, an avipox virus, an adenovirus, a herpes simplex virus (HSV) coxsackie virus, a vesicular stomatitis virus, a Newcastle disease virus, an adeno-associated virus, a polio virus, a lenti virus, a retrovirus, a reovirus, or a sindbis virus.

22. The formulation of claim 21 wherein the virus is a mature vaccinia virus.

23. The formulation of claim 15 wherein the at least one hydrophilic compound comprises at least one hydrophilic oligomer or at least one hydrophilic polymer.

24. The formulation of claim 23 wherein the at least one hydrophilic oligomer or the at least one hydrophilic polymer is selected from the group consisting of a polyalkylene oxide, a polyvinylalcohol, a polyacrylic acid, a polyacrylamide, a polyoxazoline, a polysaccharide and a polypeptide.

25. The formulation claim 24 wherein the at least one hydrophilic compound is a polyalkylene oxide.

26. The formulation of claim 15 wherein the linkage is sensitive to pH.

27. The formulation of claim 26 wherein the linkage comprises a hydrazine group.

28. A method of in vivo delivery of a virus to a region of interest, comprising:
injection into a patient a formulation comprising the virus and a synthetic enveloping composition which forms a lipid layer encompassing the virus and comprising (i) a lipid conjugate formed by conjugating at least one lipid with at least one hydrophilic compound via a linkage which is cleavable under conditions present in the region of interest (ii) a co-lipid, wherein the lipid conjugate is present in no greater than 20 mol % in the synthetic enveloping composition.

* * * * *